(12) United States Patent
Nelson et al.

(10) Patent No.: US 6,844,199 B1
(45) Date of Patent: Jan. 18, 2005

(54) DIRECT DETECTION OF BACTERIA-ANTIBODY COMPLEXES VIA UV RESONANCE RAMAN SPECTROSCOPY

(75) Inventors: Wilfred H. Nelson, Kingston, RI (US); Jay F. Sperry, PeaceDale, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 40 days.

(21) Appl. No.: 08/818,534

(22) Filed: Mar. 14, 1997

(51) Int. Cl.$^7$ .................. G01N 21/00; G01N 33/53; G01N 33/567; C12Q 1/00; G01J 3/00

(52) U.S. Cl. ................ 436/173; 356/300; 356/301; 356/302; 356/303; 356/307; 356/319; 356/326; 356/451; 435/4; 435/7.1; 435/7.2; 435/7.32; 435/7.37; 435/34; 435/38; 436/164; 436/173; 436/532; 436/804

(58) Field of Search ................ 422/82.05–82.11; 435/7.2, 7.32, 808, 962; 436/518, 805, 807

(56) References Cited

U.S. PATENT DOCUMENTS

| | | | | |
|---|---|---|---|---|
| 4,483,929 A | * | 11/1984 | Szoka | 436/533 |
| 4,822,566 A | * | 4/1989 | Newman | 422/68 |
| 4,847,198 A | * | 7/1989 | Nelson et al. | 435/34 |
| 5,126,244 A | * | 6/1992 | Muller | 435/7.31 |
| 5,266,498 A | * | 11/1993 | Tarcha et al. | 436/525 |
| 5,468,606 A | * | 11/1995 | Bogart et al. | 435/5 |
| 5,492,840 A | * | 2/1996 | Malmqvist et al. | 536/518 |
| 5,512,492 A | * | 4/1996 | Herron et al. | 436/518 |

OTHER PUBLICATIONS

Howard et al. 1980. A resonance Raman Method for the Rapid Detection and Identification of Bacteria in Water. Applied Spectroscopy. 34(1):72–75, 1980.*

Chadha et al. 1993. Ultraviolet micro–raman spectrograph for the detection of small numbers of bacterial cells. Rev. Sci. Instrum. 64(11): 3088–3093, 1993.*

Chada et al., "Ultraviolet micro–Raman spectrograph for the detection of small numbers of bacterial cells, " Reviews of Scientific Instruments, 64(11)3088–3093, Nov. 1993.*

Howard et al., "A Resonance Raman Method for the Rapid Detection and Identification of Bactera in Water, " Applied Spectroscopy, 34(1): 72–75, 1980.*

Nelson et al., "UV Resonance Raman Studies of Bacteria, " Applied Spectroscopy Reviews, 27(1): 67–124, 1992.*

Nelson et al. "UV Resonance Raman Studies of Bacteria," Applied Spectroscopy Reviews, 27(1):67–124. 1992.*

* cited by examiner

*Primary Examiner*—Lynette R. F. Smith
*Assistant Examiner*—J. Hines
(74) *Attorney, Agent, or Firm*—Gauthier & Connors LLP

(57) ABSTRACT

A system for the detection of bacteria based on bacteria-antibody complexes. Bacteria attached to antibody are detected with resonance Raman spectroscopy. The bacteria are detected directly in a great numerical excess, e.g. 100 to 10,000 of antibody molecules. A sample to be tested is placed in a medium, the medium containing antibodies attached to a surface for binding to a specific bacteria to form an antigen to antibody complex. The medium is contacted with a beam of light energy. The bacteria, as a lower resonance enhanced Raman backscattered energy, is analyzed for the presence or absence of the bacteria.

5 Claims, 1 Drawing Sheet

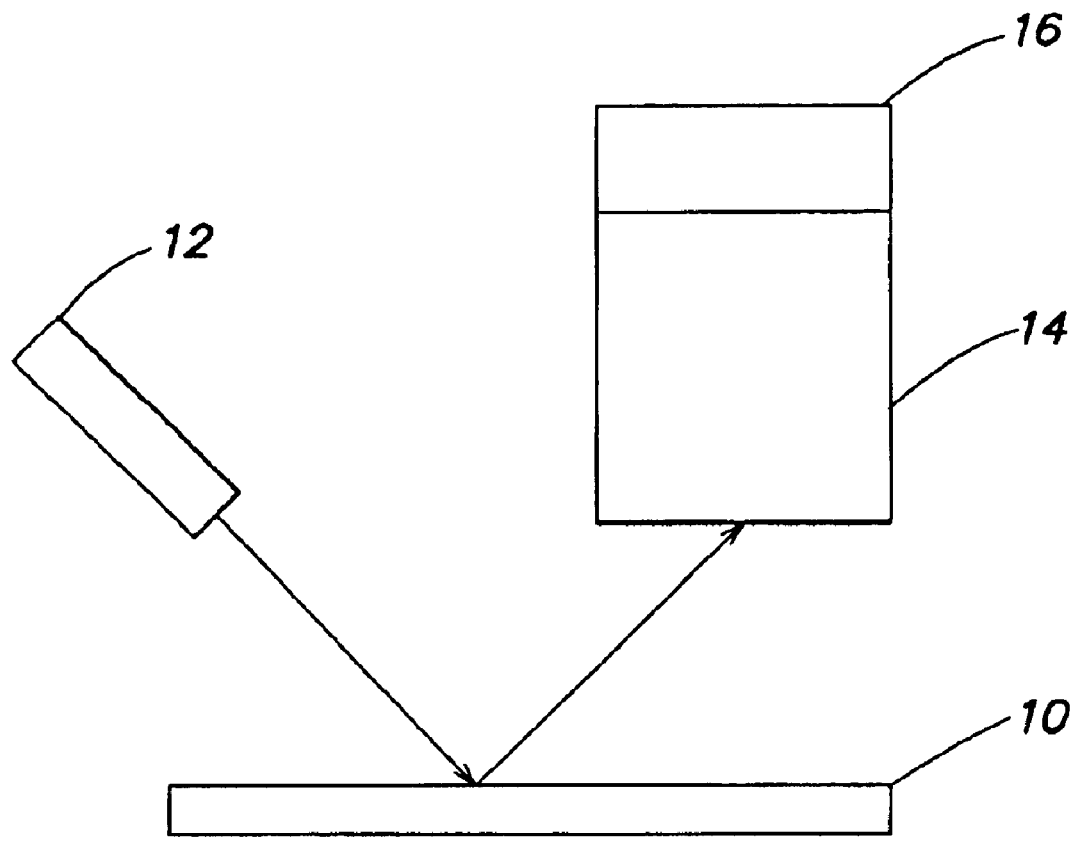
Figure

DIRECT DETECTION OF BACTERIA-ANTIBODY COMPLEXES VIA UV RESONANCE RAMAN SPECTROSCOPY

BACKGROUND OF THE INVENTION

1. Field of the Invention

The detection and identification of microorganisms using Raman spectroscopy.

2. Description of the Prior Art

There are many effective methods for the detection of microorganisms. At present, rapid, sensitive tests include fluorescent (fluorescence immunoassay or FIA), or radioactive labels (radio immunoassay or RIA) on the antibody attached in the antigen-antibody complex. Enzymes can be attached to the antibody to produce products which are more easily detected (ELISA). However, such processes (ELISA, RIA and FIA) tend to be labor intensive and not easily adapted to automation. The fluorescence method suffers from background interference and the RIA method is hampered by policies which discourage the use of radioisotopes in routine processes. If only small numbers of bacteria are present separation of the complex from the labelled antibody can be very difficult.

Among the most highly developed of the new rapid detection techniques is mass spectroscopy and its various combinations with gas chromatography (bacterial byproducts from cultures) and pyrolysis methods. Gas chromatography is highly effective in detecting characteristic bacterial metabolic products. Flow cytometry provides for the rapid detection, identification, and separation of cells. Total luminescence spectroscopy can detect organisms very rapidly. The various immunological methods also can be very specific and very rapid. All of these methods have their distinct advantages and disadvantages.

Mass spectroscopy may be unequalled in identification of pure cultures and it is very rapid and sensitive. However, it is expensive to use, requires the destruction of samples, and is of questionable use in the analysis of complex mixtures. Flow cytometry is perhaps even more costly, requires extensive sample preparation, and in many aspects is limited in its scope of applicability. Luminescence techniques are of little use except in studies of pure cultures unless combined with immunological methods. Immunological methods are unequalled in specificity and speed, as well as sensitivity. Yet, they are often impractical to use unless very expensive and perishable materials are available in a state of constant readiness. Such methods are not practical for a wide range of organisms. Gas chromatography requires that cells be grown and, hence, this method is generally slow and of limited applicability.

In bacterial analysis normally the cost effective means of analysis involves isolating organisms and then growing them in controlled cultures. This process is very slow and relatively labor intensive.

It is known to detect and identify microorganisms based on resonance Raman spectra, U.S. Pat. No. 4,847,198. A beam of visible or ultraviolet light energy contacts a microorganism under investigation. A portion of the light energy is absorbed by the microorganism and a portion of the light energy is 'emitted' from the microorganism at a lower energy level. The emitted light energy (resonance enhanced Raman scattering) can be correlated to a specific microorganism.

SUMMARY OF THE INVENTION

The present invention is directed to a system and method for detecting microorganisms with greater speed, sensitivity and specitivity than prior art methods. The need for growth of cultures is essentially eliminated. The sensitivity is much higher than rapid methods in current use (other than PCR and RIA) comparable to or better than RIA and better than FIA or ELISA since there is very little background interference and no need to purify or separate the complex.

The system and method of the invention avoids cumbersome separation steps and aids in the stabilization of the antigen-antibody complexes. This is especially true in those cases where it is necessary to detect small numbers of bacteria.

The invention is useful in environmental analysis for various consumer products, such as food products and liquid products and is useful for clinical analysis to provide rapid analysis of body fluids such as blood, spinal fluid or urine.

We have unexpectedly discovered that bacteria attached to antibody can be detected with resonance Raman spectroscopy. The bacteria can be detected directly in a great numerical excess, e.g. 100 to 10,000, of antibody molecules. This discovery results in a system and method for the rapid and low cost detection of microorganisms. The invention is based upon the formation and detection of the antigen-antibody complex. The detection of the complex is distinctly different from the prior art.

Broadly, the invention embodies a system and method for detecting microorganisms. A sample to be tested is placed in a medium, the medium containing antibodies attached to a surface for binding to a specific microorganism to form an antigen to antibody complex. The medium is contacted with a beam of light energy, some of the energy is emitted from the medium as a lower resonance enhanced Raman back-scattered energy. The presence or absence of the microorganism is detected based on a characteristic spectral peak of said microorganism.

In the preferred embodiment, there is a rinse step before spectral analysis to isolate the antigen to antibody complex.

BRIEF DESCRIPTION OF THE DRAWINGS

The FIGURE illustrates a system of the invention.

DESCRIPTION OF THE PREFERRED EMBODIMENT(S)

EXAMPLE

Bacterium, *Escherichia coli*, was grown in 50 ml of Trypticase soy broth (without glucose) in a shaking waterbath at 37° C. overnight. The bacteria were pelleted by centrifugation (12,100×g for 5 minutes at 4° C.), washed once in 20 ml of 0.85% saline and resuspended in 5 ml of 0.025M sodium phosphate buffer pH 7 to which was added 2.25–25 µl of anti-*Escherichia coli* (rabbit anti *E. coli* all ag's—purified IgG fraction 4–5 mg/ml protein, purchased from Biodesign International, Kennebunk, Maine). This was put into a continuous cycle loop, feeding through a quartz flow cell positioned in the laser beam.

Laser light 242 nm was directed into the flow cell. The emitted light energy (resonance enhanced Raman scattering) was sensed with a Raman detector. The spectrum was read and the prominent peak at 1485 cm$^{-1}$ was easily detected. The tests confirmed that the spectral characteristics of the antibody are relatively weak and do not affect the spectra of the emitted light energy from the bacteria.

Detection of about 50 complexes in the presence of great excess (200–1000 fold) of antibody molecules was achieved. The number of complexes was estimated based on laser beam geometry and known bacterial densities in the culture studied.

The formation of a single wavelength in the ultraviolet range, the use of that wavelength to create spectral information about a specimen and the control and output of that information in various graphic or tabular forms is within the scope of those skilled in the art.

The figure illustrates a flow cell 10, a laser 12, a Raman detector 14 and a display 16.

If testing for salmonella in egg yolks, a sample of the egg yolk would be taken and placed in a fluid medium such as 0.025 M phosphate buffer pH 7.2. Antibody, e.g. rabbit anti-salmonella antibodies attached to glass beads or another solid surface would then be mixed in the fluid medium. The medium would then be rinsed to remove other bacteria and contaminants and to isolate any bound antibody/salmonella complex. The isolate, preferably in aqueous medium, is placed in the cell 10. This isolate would then be scanned by the laser 12 as described above. The backscattered energy would be read by the detector 14. If the characteristic spectral peak of the bacterium were detected then the display 16 would indicate (actuate a light) the presence of salmonella in the source of the original sample.

Sensitive detection is possible because a prominent peak at 1485 cm$^{-1}$ associated with nucleic acids of bacteria can be selectively and sensitively detected in the presence of proportionately very much larger numbers of antibody if irradiation is with laser light in the range 242–257.

Previous UV spectral studies of bacteria and protein support that, if the bacteria-antibody complex can be detected using 242 nm light, that the approach will work for various wavelengths in the vicinity of 242–257 nm for which there is little protein fluorescence interference in the Raman fingerprint region, and specifically at 1485 cm$^{-1}$.

The system and method also embodies microorganism/antibodies immobilized on various surfaces, i.e. magnetic beads, which allows for the application of simple "dip-stick" or immunomagnetic processes where antibody can be directly scanned by machine methods for the presence of bacteria.

In an alternative embodiment, through use of inexpensive solar-blind coatings, analyses can be accomplished in full daylight. Since only a single peak, e.g. at 1485 cm$^{-1}$, needs to be detected, inexpensive detection methods normally used in UV filter fluorimetry can be used. This allows inexpensive optical components and simple detectors to be used.

The ability to sensitively detect bacteria in a great numerical excess of antibody results in an inexpensive means of scanning the surfaces containing immobilized antibody rapidly, sensitively and relatively inexpensively.

The suitable wavelength ranges for microorganisms and other cells are in the ultraviolet region (242–257 nm) which excites nucleotide bases of deoxyribonucleic and ribonucleic acids (DNA and RNA), as well as the aromatic amino acids of proteins (to a lesser extent).

Although the invention has been described with reference to the detection of a particular bacterium, it is equally applicable to the detection of any microorganisms or other cells that contain nucleic acids (DNA and/or RNA). Potentially, any cell that one can produce specific antibodies against for specific attachment could be detected using this detection system. In general, the common characteristics of the detection of the microorganisms is the presence of specific chemicals in their macromolecules, which when struck with an incident beam of light energy, particularly ultraviolet energy, emits very characteristic spectra.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope the invention.

Having described our invention, what we now claim is:

1. A method for detecting the presence of a specific microorganism in a sample, the microorganism having a characteristic resonance enhanced Raman backscattered energy spectrum produced by irradiating nucleic acids in the microorganism at a wavelength between 242–257 nm, the method comprising:

(a) contacting the sample with a medium comprising solid phase immobilized antibodies which specifically bind to a characteristic cell surface antigen on the microorganism to form an antigen-antibody complex, thereby immobilizing the microorganism on the solid phase;

(b) irradiating the solid phase of step (a) with a laser light of 242–257 nm to produce a resonance enhanced Raman backscattered energy; and (c) comparing the induced spectrum of step (b) with said characteristic spectrum to detect the presence of the microorganism in the sample, when at least a 200:1 ratio of solid phase immobilized antibodies in the medium to microorganism in the sample exists.

2. The method of claim 1 wherein the medium is a fluid medium and the microorganism is a bacterium.

3. The method of claim 2 wherein the bacterium is *E.coli* and the antibodies are anti-*E.coli*.

4. The method of claim 1 wherein the solid phase of step (a) is washed to remove unbound sample and medium before the irradiating step (b).

5. The method of claim 1 wherein the characteristic spectrum is at 1485 cm$^{-1}$.

* * * * *